US008397332B2

(12) United States Patent
Kraus et al.

(10) Patent No.: US 8,397,332 B2
(45) Date of Patent: Mar. 19, 2013

(54) ELECTRIC TOOTHBRUSH

(75) Inventors: Bernhard Kraus, Braunfels (DE);
Frank Ziegler, Frankfurt am Main (DE);
Uwe Schober, Glashütten (DE); Robert Schäfer, Frankfurt am Main (DE);
Christian Neyer, Eschborn (DE)

(73) Assignee: Braun GmbH, Kronberg (DE)

( * ) Notice: Subject to any disclaimer, the term of this patent is extended or adjusted under 35 U.S.C. 154(b) by 514 days.

(21) Appl. No.: 12/601,877

(22) PCT Filed: Jun. 11, 2008

(86) PCT No.: PCT/EP2008/004645
§ 371 (c)(1),
(2), (4) Date: Nov. 25, 2009

(87) PCT Pub. No.: WO2009/000418
PCT Pub. Date: Dec. 31, 2008

(65) Prior Publication Data
US 2010/0175207 A1    Jul. 15, 2010

(30) Foreign Application Priority Data

Jun. 28, 2007  (DE) .......................... 10 2007 029 972

(51) Int. Cl.
*A61C 17/32*  (2006.01)
*A61C 17/34*  (2006.01)
*A61C 17/40*  (2006.01)
*A61C 17/22*  (2006.01)

(52) U.S. Cl. ......................................... 15/22.1; 15/22.4

(58) Field of Classification Search ............... 15/22.1, 15/22.4; 132/308–311; *A61C 17/22, 17/24, A61C 17/26, 17/32, 17/34, 17/40*
See application file for complete search history.

(56) References Cited

U.S. PATENT DOCUMENTS

| | | | | | |
|---|---|---|---|---|---|
| 4,149,291 | A | * | 4/1979 | Stoltz .............................. | 15/22.1 |
| 4,175,299 | A | * | 11/1979 | Teague et al. .................. | 15/22.1 |

(Continued)

FOREIGN PATENT DOCUMENTS

| | | |
|---|---|---|
| DE | 29 31 479 | 2/1981 |
| DE | 10 2004 036812 A1 | 3/2006 |

(Continued)

OTHER PUBLICATIONS

PCT International Search Report dated Sep. 29, 2008.

*Primary Examiner* — Robyn Doan
*Assistant Examiner* — Tatiana Nobrega
(74) *Attorney, Agent, or Firm* — John P. Colbert; Jay A. Krebs

(57) ABSTRACT

The present invention relates to an electric toothbrush, specifically the toothbrush handle of an electric toothbrush, with a handle housing, with a preferably rod-shaped drive transmitter which protrudes from a first side of the handle housing and on which a brush attachment can be secured, and with a drive motor for moving the drive transmitter, wherein the drive transmitter is mounted, by means of a bearing device in the interior of the handle housing, in the manner of a rocker arm such that the drive transmitter can be pivoted to-and-fro transverse to its longitudinal axis by the drive motor. The invention further relates to the whole toothbrush, comprising such a toothbrush handle part and a brush attachment secured to the drive transmitter thereof. According to the invention, the bearing device holds the drive transmitter so as to pivot about a rotation point lying outside the handle housing. Said rotation point is offset particularly far out from the handle housing, such that it comes to lie between the bristle array of the brush attachment and the front end of the handle in the area of the lips. In this way, an efficient cleaning movement with a large cleaning amplitude in the area of the bristle array can be combined with a low vibration amplitude of the toothbrush in the area of the lips.

22 Claims, 3 Drawing Sheets

U.S. PATENT DOCUMENTS

Figure 1:
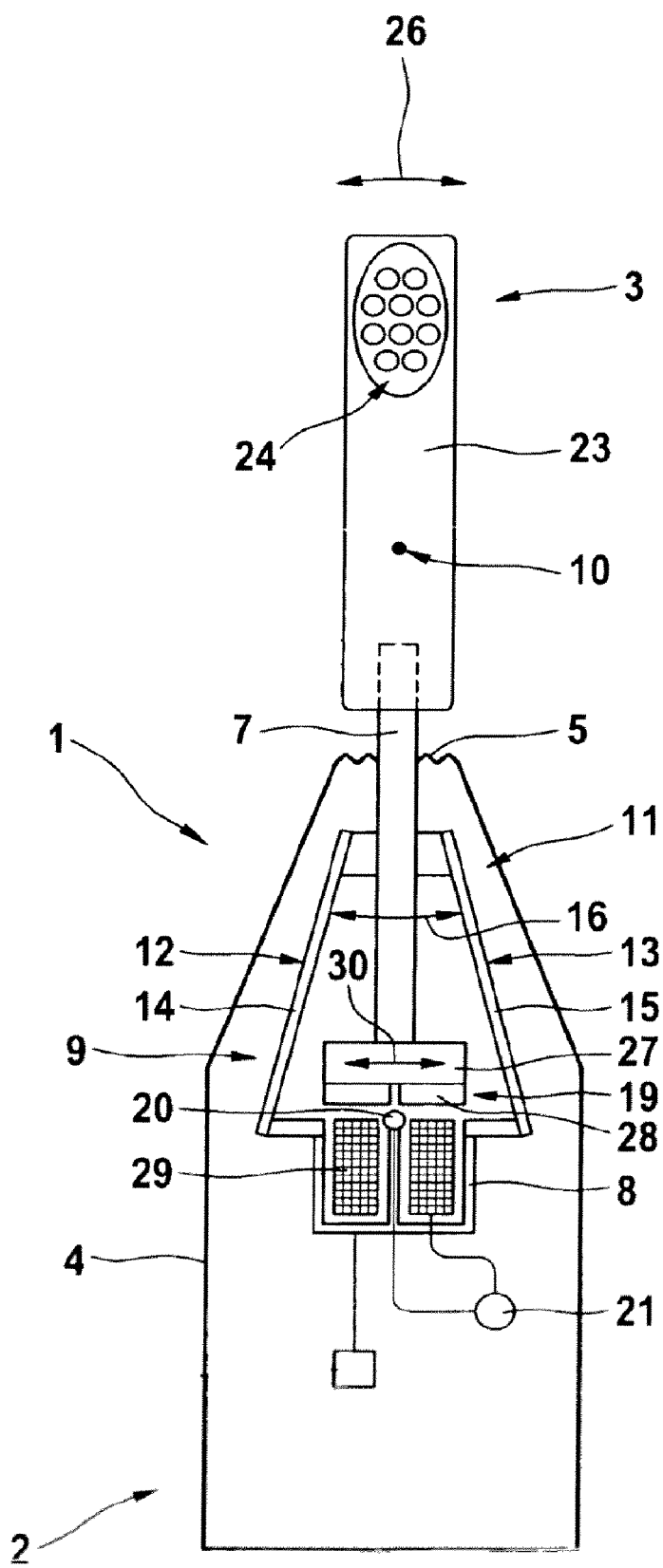

| | | | | |
|---|---|---|---|---|
| 4,698,869 A * | 10/1987 | Mierau et al. | | 15/22.1 |
| 4,974,278 A * | 12/1990 | Hommann | | 15/22.1 |
| 5,189,751 A * | 3/1993 | Giuliani et al. | | 15/22.1 |
| 5,263,218 A * | 11/1993 | Giuliani et al. | | 15/22.1 |
| 5,406,664 A * | 4/1995 | Hukuba | | 15/22.1 |
| 5,448,792 A * | 9/1995 | Wiedemann et al. | | 15/22.1 |
| 5,504,959 A * | 4/1996 | Yukawa et al. | | 15/22.1 |
| 5,613,259 A * | 3/1997 | Craft et al. | | 15/22.1 |
| 5,784,742 A * | 7/1998 | Giuliani et al. | | 15/22.1 |
| 6,140,723 A * | 10/2000 | Matsui et al. | | 310/81 |
| 6,453,498 B1 * | 9/2002 | Wu | | 15/22.1 |
| 6,739,012 B2 * | 5/2004 | Grez et al. | | 15/22.1 |
| 6,836,918 B1 * | 1/2005 | Wong | | 15/22.1 |
| 7,150,061 B2 * | 12/2006 | Kwong | | 15/22.1 |
| 7,162,764 B2 * | 1/2007 | Drossler et al. | | 15/22.1 |
| 7,219,384 B2 * | 5/2007 | Hohlbein | | 15/22.1 |
| 7,315,098 B2 * | 1/2008 | Kunita et al. | | 310/15 |
| 7,386,904 B2 * | 6/2008 | Fattori | | 15/22.1 |
| 7,979,939 B2 * | 7/2011 | Hilscher et al. | | 15/22.1 |
| 2002/0129454 A1 * | 9/2002 | Hilscher et al. | | 15/22.1 |
| 2003/0154567 A1 * | 8/2003 | Drossler et al. | | 15/22.1 |
| 2004/0154113 A1 * | 8/2004 | Drossler et al. | | 15/22.1 |
| 2005/0146296 A1 * | 7/2005 | Klemm et al. | | 318/119 |
| 2005/0235438 A1 * | 10/2005 | Motohashi et al. | | 15/22.1 |
| 2006/0225230 A1 * | 10/2006 | Choung et al. | | 15/22.1 |
| 2006/0254007 A1 * | 11/2006 | Banning | | 15/28 |
| 2006/0255665 A1 * | 11/2006 | Kraus et al. | | 310/36 |
| 2007/0124877 A1 * | 6/2007 | Lee | | 15/22.1 |
| 2008/0185922 A1 * | 8/2008 | Kressner et al. | | 310/36 |
| 2009/0019651 A1 * | 1/2009 | Grez et al. | | 15/22.1 |
| 2012/0024323 A1 * | 2/2012 | Klemm et al. | | 134/18 |

FOREIGN PATENT DOCUMENTS

| | | |
|---|---|---|
| DE | 10 2005 045 226 A1 | 3/2007 |
| WO | WO 03/024353 A | 3/2003 |
| WO | WO 2005/058189 | 6/2005 |
| WO | WO 2005058189 A1 * | 6/2005 |

* cited by examiner

ELECTRIC TOOTHBRUSH

The present invention relates to electric toothbrushes, specifically the toothbrush handle of an electric toothbrush, with a handle housing, with a preferably rod-shaped drive transmitter which protrudes from a first front of the handle housing and on which a brush attachment can be secured, and with a drive motor for moving the drive transmitter, wherein the drive transmitter is mounted, by means of a bearing device in the interior of the handle housing, in the manner of a rocker arm such that the drive transmitter can be pivoted to-and-fro transverse to its longitudinal axis by the drive motor. The invention further relates to the whole toothbrush, comprising such a toothbrush handle part and a brush attachment.

In order to support the important cleaning movement in the longitudinal direction of the teeth, i.e. parallel to the interfacial areas between adjoining teeth, electric toothbrushes have already been proposed in which the bristle array is driven transverse to the longitudinal direction of the brush tube and transverse to the main bristle direction of the bristle array. To this end, a conventional, rod-shaped drive transmitter, which typically protrudes from the front of the handle housing, can be driven by an electromechanical actuator transverse to the longitudinal axis of the drive transmitter, such that a brush attachment secured on the drive transmitter executes the desired cleaning movement in the form of an oscillation movement.

A number of different drives are known for so-called ultrasonic toothbrushes. With some drives, bearings, for example ball bearings, are used to support the drive transmitter; however, this is expensive and complex and, in addition, often leads to unpleasant noises as well as damping of the motor. With other drives, springs are used to support the drive transmitter; however, this can involve a complex and expensive construction, particularly in the brush attachments.

US 2006/0225230 A1 discloses a toothbrush in which the bristle array can be driven to-and-fro transverse to the longitudinal direction of the toothbrush. To that end, a relatively complicated drive mechanism, with multiple gearwheel stages and a wobble plate is provided, which converts the rotational drive movements of an electric motor into the desired to-and-fro cleaning movement of the brush attachment.

Furthermore, DE 29 31 479 discloses a drive transmission, which converts a rotational movement into a to-and-fro tipping movement. Even though this document also mentions toothbrushes as an area of application, the gearing mechanism is constructed in a bulky manner to the extent that integration into a slim toothbrush body is hardly possible.

An essential problem of such toothbrushes with a translatory transverse movement of the bristle array is also the fact that the transverse movement does not just occur on the bristle array but also in the area of the brush tube, which, on one hand, can cause unpleasant sensations for users in the area of the incisors and the lips, and, on the other hand, can also be associated with undesirable drive damping as well as problems with generating sufficient movement amplitudes.

Starting from this point, the object of the present invention is to create an improved toothbrush of the type mentioned as well as an improved toothbrush handle, which will avoid the disadvantages of the prior art and build upon the latter in an advantageous manner In particular, a drive with particularly simple and economical construction should be provided, which will produce an efficient cleaning movement in the area of the bristle array and thereby a high cleaning performance, despite having low vibration amplitude in the area of the lips.

Said object is achieved by a toothbrush handle according to Claim 1 as well as a toothbrush according to Claim 18. Preferred embodiments of the invention are the subject matter of the dependent claims.

Thus, it is proposed that, despite support of the drive transmitter in the interior of the handle housing, the movement center of the rocker or pivot movement of the drive transmitter and the attachment brush mounted thereon be relocated away from the handle housing in the direction of the bristle array and, in particular, to a section of brush tube lying approximately in the area of the lips when the teeth are cleaned, such that the bristle array can pivot or oscillate around the movement center mentioned, without the brush tube executing any or only a slight movement in the area of the lips. According to the invention, the bearing device holds the drive transmitter so as to pivot about a rotation point lying outside the handle housing. In this way, an efficient cleaning movement with a large cleaning amplitude in the area of the bristle array can be combined with a low vibration amplitude of the toothbrush in the area of the lips. Said rotation point is relocated particularly away from the handle housing, such that it preferably comes to lie between the bristle array of the brush attachment and the front end of the handle in the area of the lips of a user.

The bearing device for the drive transmitter can be designed in different ways. According to an advantageous embodiment of the invention, the bearing device can comprise a multi-jointed suspension, preferably in the form of a fourfold joint with two bearing legs, each of which are mounted, as a joint, to the drive carrier on one end and mounted, as a joint, to the handle housing or to a part fixedly mounted to the handle housing, such as, for example, a motor group carrier, on the other end. The multi-jointed suspension in this case is designed, with respect to its kinematics, such that it defines the so-called rotation point outside the handle housing. Advantageously, the suspension in this case can be constructed in the form of a simple fourfold joint, the bearing legs of which have rotational axes that are essentially parallel to one another.

Preferably, the bearing device for the drive transmitter can comprise two simple spring elements, for example compound springs, which retain the drive transmitter in the manner of a fourfold joint and thus with one end of each mounted to the drive transmitter and with the other end mounted to the handle housing or to a part fixedly mounted to the handle housing. In general, other flexible spring elements, for example in the form of rod-shaped flexible springs, can be used instead of compound springs, wherein, however, compound springs, with their different levels of stiffness in different directions are preferred and are particularly suitable for the suspension of the drive transmitter. Due to the flexible, elastic design, the compound springs in this case do not need to be supported as a joint but rather can be rigidly mounted at their ends, wherein a particularly economical design can result therefrom if the shape of the compound springs conforms to that of the drive transmitter, said retaining connecting piece, a drive motor carrier, and/or a housing part, particularly if the compound springs are injection-molded and made of plastic. Due to the suspension of the drive transmitter by means of compound springs, a particularly simple design of the suspension for the drive transmitter can be achieved, regardless of the design of the aforementioned rotational point for the drive transmitter, while still maintaining favorable kinematics in the drive movement. In addition, damping problems can be avoided to a large extent, regardless of a certain position of the rotational point.

The dimensioning of the compound springs and/or the bearing legs of the fourfold joint and their arrangement and alignment can essentially be adapted to the design of the toothbrush handle and/or the brush attachment, wherein, depending on the configuration of the case at hand, for example, the length of the compound springs and/or the bearing legs, the positioning of the pivot points, and/or the angle alignment of the leaf springs and/or the bearing legs can be changed spatially. According to an advantageous embodiment of the invention, the bearing legs and/or the leaf springs can be arranged at a steep angle with respect to one another, so that the longitudinal axes converge at the movement center of the drive transmitter and/or the brush attachment mounted thereon. In particular, the bearing legs and/or the compound springs can be arranged in a manner so as to proceed at a tilt with respect to one another such that the intended extension lines through the longitudinal axes of the bearing legs or the compound springs define an intersection on the longitudinal axis of the drive transmitter, outside the handle housing, wherein the intersection does not necessarily have to be on the drive body itself but rather can, optionally, also lie on the drive transmitter's longitudinal axis extending virtually beyond it.

The tilt angle of the bearing legs or the compound springs in this case can advantageously be in an angle range of between 10° and 75°, preferably between 15° and 45°, and particularly approximately in the range of from 20° to 40°.

In a further embodiment of the invention, the bearing legs of the multi-joint or the aforementioned compound springs are arranged lying in a common plane, which forms the bearing plane of the bearing device and/or that define the movement plane of the bearing legs or the flexing spring elements, in which the aforementioned bearing legs or spring elements execute their movement.

The drive motor coupled to the drive transmitter can, itself, be designed in different ways. For example, the rotational movement of a rotating electric motor can be converted, via a coupling element or the like, into a to-and-fro movement and transmitted to the drive transmitter. In a preferred embodiment of the invention however, the drive motor is designed as a linear motor, preferably a magnetic oscillation motor, which immediately generates a linear to-and-fro movement, which is transmitted to the drive transmitter. The drive movement of the drive motor in this case advantageously lies in a drive plane; in particular, it can be designed as a single axis.

In order to generate a planar rocking movement of the drive transmitter and the brush attachment mounted thereon, the drive motor, in a further embodiment of the invention, is designed in such a manner that its drive plane or its linear drive axis extends parallel to the aforementioned bearing plane, in which the bearing legs or the spring elements of the bearing device are arranged. The drive transmitter hereby rocks in a plane parallel to the drive movement of the drive motor.

Alternatively however, a spatial drive movement of the drive transmitter can also be generated. In particular, the drive transmitter can move on a drive track, which is essentially shaped as a double cone, despite use of a linear motor as the drive motor. To this end, the drive plane of the drive motor can be steeply tilted as compared to the aforementioned bearing plane of the bearing device in which the bearing legs of the multi-joint or the compound springs of the bearing device are arranged, wherein a tilting of less than 45° is preferable. This generates a so-called spatial rocking movement of the drive transmitter on a drive track, which is essentially shaped as a double cone, preferably with an elliptical cross-section to the cone. The drive transmitter's rotational point mentioned at the beginning forms the restriction of the aforementioned double-cone-shaped drive track, wherein the rotational point itself does not have to be a point actually fixed in space, but may even circulate on a movement track, which, however, is extensively smaller than the movement amplitude of the bristle array.

Preferably, the drive transmitter, along with the brush attachment mounted thereon and, optionally, further moving oscillating parts, such as drive magnets, coupling pieces, etc., form a drive train capable of oscillating, wherein, in a particularly advantageous manner, the resonance frequency of the drive train is synchronized with the oscillation frequency of the motor or vice versa. The oscillation system can be designed in a manner such that the bristle array of the brush attachment and the drive motor oscillate in phase opposition or phase equalization, wherein, in the latter case, two oscillating nodes are present along the drive train, which comprises the brush attachment and the drive transmitter. Advantageously in this case, the suspension is selected via the aforementioned flexible spring elements and/or compound springs such that the rotational point defined by the spring elements lies in one of the node points. The other node point can advantageously lie in the area of the brush attachment in the area of the lips, wherein, in this case, the aforementioned rotational point does not lie in the area of the lips but rather closer to the toothbrush handle. The spring elements can serve as resonance springs of the oscillation system.

By means of the aforementioned multi-joint or flexible-spring suspension of the drive transmitter, the pressing force occurring when the teeth are cleaned can be determined in a simple manner, i.e. the press-on force that a user utilizes to press the toothbrush against the teeth. In particular, in a further embodiment of the invention, a transverse load recording device can be allocated to the drive transmitter and/or the drive motor. By means of the suspension of the drive transmitter, a relative deflection of the drive motor or its drive element occurs when pressure is applied to the bristle array and this deflection can be easily measured, in particular, by means of a magnetic field sensor.

The transverse load recording can be used, in an advantageous manner, to activate the drive motor. To that end, a control device connected to the transverse load recording device is provided, which, in particular, controls the oscillation amplitude and/or the oscillation frequency of the drive motor, as a function of the press-on force recorded. For example, in the event of excessive press-on force of the bristle array onto the teeth, the oscillation amplitude and/or the oscillation frequency can be slowed down, or optionally even stopped completely. As an alternative or in addition, the control device can activate a display that shows the user the press-on force being exerted or that warns the user when the force used for cleaning is excessive. As a further alternative or in addition, the control device can also bring about a start control, as a function of the transverse load recorded, particularly to the extent that the drive motor is started automatically when a certain press-on force is present and/or maintained over a certain time.

Figure 2:
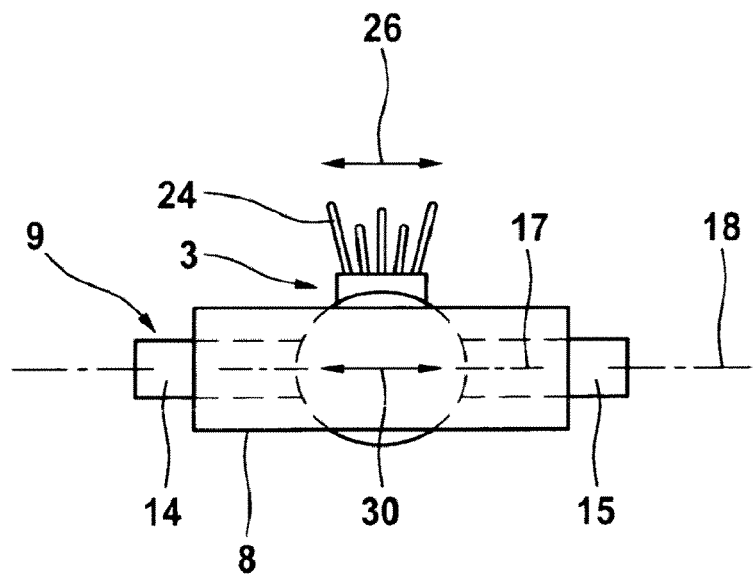
Figure 3:
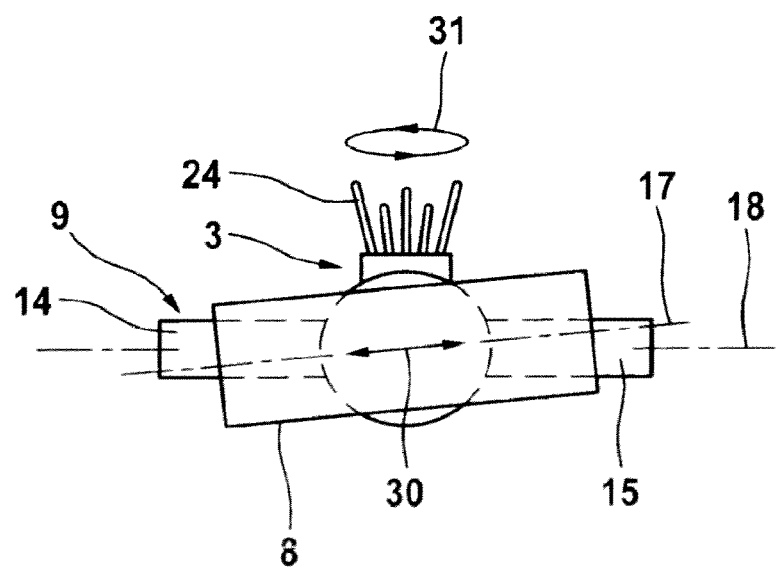
Figure 4:
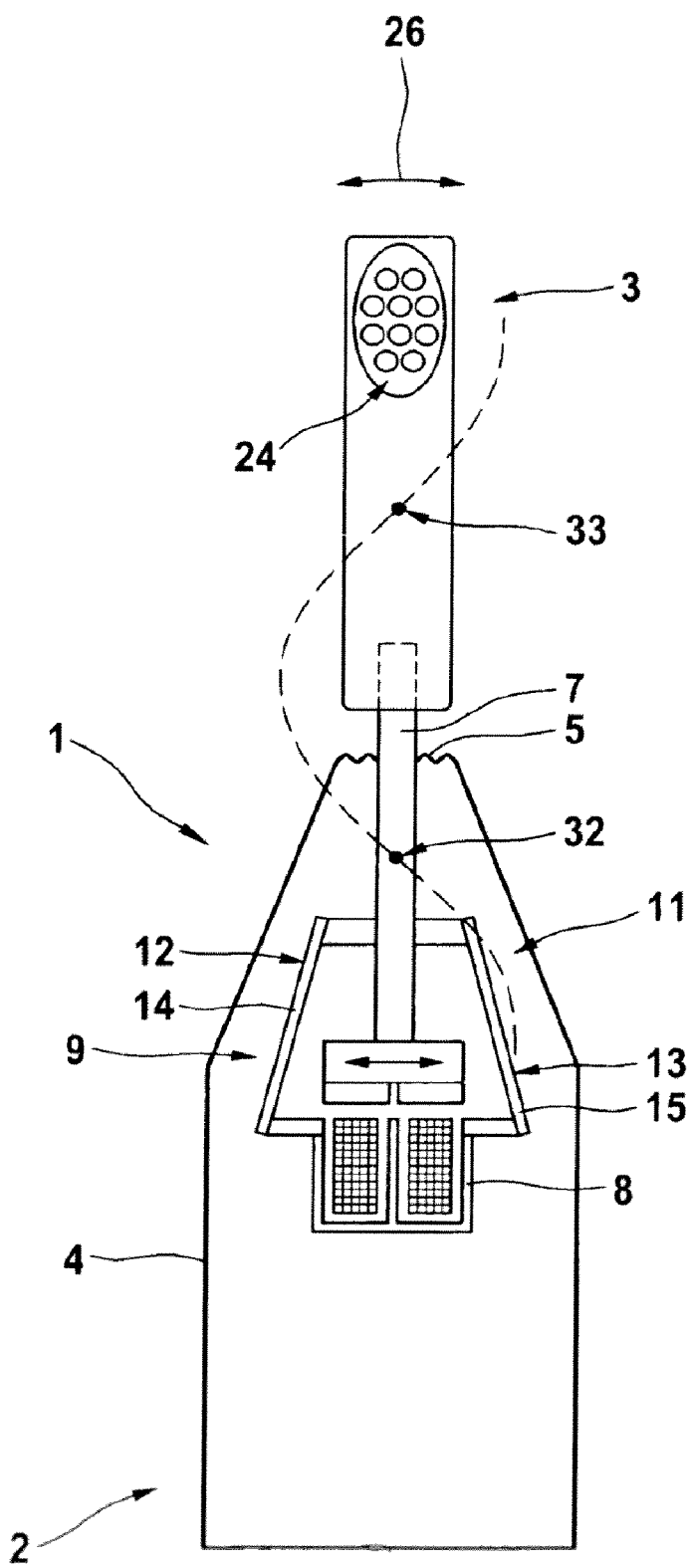

The invention is illustrated in more detail in the following by means of preferred exemplary embodiments and corresponding drawings. The drawings show the following:

FIG. 1: is a schematic top view of an electric toothbrush, according to an advantageous embodiment of the invention, which shows the suspension of the drive transmitter and of the drive motor that drives it;

FIG. 2: is a schematic view of the suspension of the drive transmitter and of the drive motor when viewed in a direction that is parallel to the longitudinal axis of the toothbrush, wherein the drive motor, with its drive plane, is arranged parallel to the bearing plane of the suspension, in order to generate a planar rocking movement of the brush attachment;

FIG. 3: is a schematic view of the suspension of the drive transmitter and of the drive motor when viewed in a direction that is parallel to the longitudinal axis of the toothbrush, similar to FIG. 2, wherein, according to FIG. 3, the drive plane of the drive motor is tilted in relation to the bearing plane of the suspension of the drive transmitter, in order to generate an elliptical movement path of the bristle array of the brush attachment; and FIG. 4: is a schematic top view of a toothbrush similar to FIG. 1 according to a further preferred embodiment of the invention, according to which the drive train forms a resonance oscillating body, wherein, in the representation, the two oscillation nodes that form along the drive train are shown.

The toothbrush 1 shown in FIG. 1 comprises a longitudinal, essentially rod-shaped toothbrush handle 2, as well as a brush attachment 3 that can be placed on the toothbrush handle 2, wherein the brush attachment 3 has an essentially rod-shaped brush 23 as well as a bristle array 24 mounted thereon comprising a plurality of bristle bushes.

The brush attachment 3 is rigid, but removably attached to a rod-shaped drive transmitter 7, which protrudes from the first front 5 of the handle housing 4 of the toothbrush handle 2. The interior of the handle housing 4 accommodates a drive motor 8, a power supply 25 supplying the drive motor 8, for example in the form of a power unit or a energy storage unit such as batteries, as well as a control device 21 to activate the drive motor 8.

As shown in FIG. 1, the drive transmitter 7 extends some distance into the handle housing 4, wherein, in the embodiment shown, the section of the drive transmitter 7 lying inside the handle housing 4 has a larger length than the section of the drive transmitter 7 extending beyond the first front 5 of the handle housing 4. A bearing device 9 is provided for in the interior of the handle housing 4 for the drive transmitter 7; the bearing device 9 supports the drive transmitter 7 in a moving manner such that the drive transmitter 7 can execute transverse movements transverse to its longitudinal axis and, in particular, tilt or rocking movements around an axis that is vertical with respect to the drawing plane of FIG. 1, such that the bristle array 24 of the brush attachment 3 mounted thereon can oscillate, to-and-fro, transversely with respect to the longitudinal axis of the brush attachment and transverse to the primary direction of the bristles, which is vertical to the drawing plane of FIG. 1. The bristle array movement direction indicated in FIG. 1 with reference number 26 corresponds to an up-and-down wiping along the tooth flanks that is essentially parallel to the areas between the teeth.

In the embodiment shown in FIG. 1, the bearing device 9 comprises two tilted compound springs 14, 15, which are fixedly connected to the drive transmitter 7 on one end and rigidly attached to a point fixedly mounted to the handle housing on the opposing other end, for example to a motor carrier group, which is not shown in the drawing. The compound springs 14 and 15 in this case form the bearing legs 12 and 13 of a fourfold joint 11, through which the drive transmitter 7 can move to-and-fro in the bearing plane 18, which corresponds to the drawing plane of FIG. 1 and is tensioned by the two compound springs 14 and 15. By means of the bearing device 9 designed in the form of a fourfold joint, the latter defines a virtual rotational point 10 for the drive transmitter 7, wherein the rotational point 10 lies outside the handle housing 4 despite arrangement of the bearing device 9 on the inside of the handle housing 4, specifically between the first front 5 of the handle housing 4 and the bristle array 24 of the brush attachment 3. Advantageously, the arrangement of the bearing device 9 is carried out in a manner such that the aforementioned rotational point 10 lies, in a loose sense, in the center section of the brush tube 23, which lies approximately in the area of the lips when the teeth are cleaned. This results in only a small movement amplitude of the brush attachment 3 in the area of the lips, whereas a large movement amplitude and thereby an efficient cleaning movement results in the area of the bristle array 24.

The drive transmitter 7 and the brush attachment 3 mounted thereon are namely pivoted to-and-fro, around the aforementioned rotational point 10, in the manner of a rocker. Advantageously, the drive motor 8 is designed as a linear motor in the form of a magnetic oscillating motor, which has a drive piece 27 that moves linearly to-and-fro. FIG. 1 schematically shows the design of the drive motor 8 in the form of two magnets 28 and corresponding coils 29, which move the magnets 28 to-and-fro with the corresponding stimulation, wherein the magnets 28, in turn, linearly move the drive piece 27 to-and-fro according to the movement arrow 30. The linearly drivable drive piece 27 is coupled to the end of the drive transmitter 7 lying in the handle housing 4, such that said drive transmitter 7 is accordingly moved to-and-fro, whereby a corresponding pivot movement results around the rotational point 10.

As shown in FIG. 2, the drive planes 17, in which the movement direction of the drive piece 27 lies, can advantageously be parallel to the aforementioned bearing plane 18, which is tensioned by the compound springs 14 and 15. This results in a two-dimensional rocking movement of the drive transmitter 7 in the aforementioned bearing plane 18.

As an alternative to this, the drive motor 8, with its drive plane 17, can also be tilted with respect to the aforementioned bearing plane 18, as shown in FIG. 3. Accordingly, the movement direction 30 of the drive piece 27 proceeds at a steep angle with respect to the aforementioned bearing plane 18 of the bearing device 9, wherein the tilt angle between the drive plane 17 and the bearing plane 18 can be advantageously less than 45°, preferably less than 25°. The aforementioned tilting generates a spatial drive movement of the drive transmitter 7, which oscillates around the rotational point 10 on a double-cone-shaped drive track, wherein, depending on the tilt angle of the drive plane 17, the cross-section of the aforementioned double cone is more or less pressed flat. The very slight tilting, which is shown in FIG. 3, results in an elliptical circulatory movement of the bristle array 24, as is indicated by reference number 31, cf. FIG. 3. As a result, the bristle array 24 takes on a picking movement, which is essentially vertical to the tooth flanks, in addition to the wiping movement along the tooth flanks, and said picking movement enables improved penetration of the bristles into the areas between the teeth.

The position of the virtual rotational point 10 is advantageously selected such that the vibration is minimal in the toothbrush handle 2. To this end, the rotational point 10 is advantageously moved to the center of mass of the oscillation system formed by the moving parts of the toothbrush. Advantageously, the masses of the drive train, which comprise the brush attachment 3, the drive transmitter 7, the drive piece 27 mounted thereon, and the magnets 28, are distributed in a manner such that the center of mass of the oscillating drive train lies in the area of the brush tube 23 of the brush attachment 3 and, in particular, in the area of the rotational point 10.

It is advantageous to select the stiffness of the aforementioned drive train such that the drive train, comprising the brush attachment 3, the drive transmitter 7, the drive piece 27 of the drive motor 8, and its magnets 28 moving to-and-fro, has a resonance frequency, which is synchronized to the frequency at which the motor is electrically driven. In actuality, the drive train has multiple resonance frequencies. Therefore, with a corresponding activation of the motor, it is possible for the brush attachment 3 and the magnet 28 of the drive motor 8 to oscillate in phase equalization, wherein two oscillating nodes form along the drive train, as indicated in FIG. 4. Advantageously, the suspension the compound springs 14 and 15 is selected such that the virtual rotational point 10, which is defined by the arrangement of the bearing device 10 in the manner of a fourfold joint, lies in one of the oscillating nodes 32, whereas the other oscillating node 33 lies in the area of the brush attachment 3, which lies approximately in the area of the lips when the teeth are being cleaned.

The activation of the drive motor 8 by the control device 21 can be designed in different ways. Advantageously, the activation of the drive motor 8 can occur with a constant frequency, which can be achieved through very minor technical switching efforts. Advantageously, as the supply voltage drops, for example as the batteries become weaker, the activation impulses can be broadened in order to keep the vibration amplitude constant. In a further embodiment of the invention, the motor amplitude can be measured by means of the voltage induced by the motor or a motor amplitude sensor and constantly regulated as a function of said measurement signal.

In a further embodiment of the invention, the control device 21 is connected to a transverse load recording device 19, which records a load acting transversely on the drive transmitter 7 and consequently the press-on forces of the toothbrush during cleaning. By means of the described suspension of the drive transmitter 7 through the bearing device 9, a relative deflection of the magnet 28 of the drive motor 8 occurs when pressure is applied to the brush attachment 3; said relative deflection can be easily measured, for example, by means of a magnetic field sensor 20. The signal of the magnetic field sensor 20, which indicates the press-on force of the toothbrush during cleaning, can be used by the control device 20 in various ways. For example, a user display, which is not shown in more detail, can be activated in order to give the user a signal when excessive press-on pressure is being applied. Advantageously, the control device 21 can also reduce the motor amplitude when there is excessive press-on pressure. In addition, the control device 21 can actualize an automatic start, which does not activate the drive motor 8 until a certain press-on pressure is present for a certain period of time.

The tilted position of the compound springs 14 and 15 can be adapted to the design of the toothbrush handle 2 and the brush attachment 3, in particular to their dimensions and mass distribution. In the embodiment shown in FIG. 1, the angle 16 between the compound springs 14 and 15 is between 20° and 40°, whereby when the compound springs 14 and 15 are arranged in the front third of the handle housing 4, the desired position of the rotational point 10 outside the handle housing 4, in the area of the brush tube 23 of the brush attachment 3, is achieved.

Due to the suspension of the drive transmitter 7 as proposed by the present invention and the design of the drive motor 8 allocated to said drive transmitter 7 in the form of a simple linear drive, considerable advantages are achieved. Only minor vibrations occur in the handle, wherein a large cleaning amplitude is achieved in the area of the brush array, while simultaneously only a small oscillation amplitude is present in the area of the lips. The frequency can essentially be controlled independently of the operating voltage and independently of the load, aging, temperature, or other influences. A relatively stable amplitude can be achieved without particular control measures; in addition, the amplitude and frequency of the oscillation movement of the brush attachment can be adjusted very easily and independently of one another. This makes different operating modes possible such as, for example, soft mode or massage mode. Moreover, the simple motor design is characterized by favorable manufacturing costs and by a compact construction at the same time.

What is claimed is:

1. A toothbrush handle of an electric toothbrush, with a handle housing having a rod-shaped drive transmitter which protrudes from a first front of the handle housing including a drive motor for moving the drive transmitter wherein the drive transmitter is mounted, by means of a bearing device comprising bearing legs or spring elements in the interior of the handle housing, in the manner of a rocker arm such that the drive transmitter can be pivoted to-and-fro transverse to its longitudinal axis by the drive motor, wherein the drive transmitter is held by the bearing device in a manner so as to swivel around a rotational point, which lies outside the handle housing wherein the rotational point is a distance away from the first front of the handle housing which is longer than the protrusion of the drive transmitter, which extends beyond the first front of the handle housing and/or is less than a total length of the handle housing and wherein the bearing legs or spring elements are arranged, on opposing sides of the drive transmitter, at a steep angle with respect to one another, tilted toward the rotational point of the drive transmitter and converging with one another.

2. The toothbrush handle according claim 1, wherein the bearing device includes a multi-jointed suspension in the form of a fourfold joint, with two bearing legs, one end of which is mounted, as a joint, to the drive transmitter and the other end of which is mounted, as a joint, to the handle housing or to a part fixedly mounted to the handle housing.

3. The toothbrush handle according to claim 1, wherein the bearing device comprises two spring elements which support the drive transmitter in the handle housing in the form of a fourfold joint, wherein one end of which is mounted to the drive transmitter and other end is mounted to the handle housing or to a part fixedly mounted on the handle housing.

4. The toothbrush handle according to the preceding claim 1, wherein the bearing legs or spring elements are tilted with respect to one another such that the intended extension lines through the longitudinal axes of the bearing legs or spring elements define an intersection on the longitudinal axis of the drive transmitter outside the handle housing.

5. The toothbrush handle according to claim 4, wherein the bearing legs or spring elements form an angle with respect to one another, which is between 10° and 60°.

6. The toothbrush handle according to claim 1, wherein the drive motor has a means for generating a linear to-and-fro drive movement in a drive plane.

7. The toothbrush handle according to the preceding claim 6, wherein the drive motor is designed as a linear motor.

8. The toothbrush handle according to claim 2, wherein a drive plane of the drive motor, lies parallel to a bearing plane of the drive transmitter, in which the bearing legs or spring elements of the bearing device are arranged.

9. The toothbrush handle according to claim 6, wherein the drive transmitter is supported by the bearing device in a manner which allows three-dimensional movement and the drive transmitter can be spatially driven by the drive motor on a double-cone shaped drive track.

10. The toothbrush handle according to claim 2, wherein a drive plane of the drive motor is steeply tilted as compared to a bearing plane of the bearing device, in which the bearing legs or spring elements of the bearing device are arranged.

11. The toothbrush handle according to claim 1, wherein a transverse load recording device is allocated to the drive transmitter or to the drive motor to record a toothbrush press-on force.

12. The toothbrush handle according to the claim 11, wherein the transverse load recording device has a means for recording a load of a drive motor.

13. The toothbrush handle according to claim 12, wherein the transverse load recording device has a magnetic field sensor for recording a magnetic field found in the drive motor.

14. The toothbrush handle according to claim 11, wherein a control device for activating the drive motor is provided as a function of a signal of the transverse load recording device.

15. The toothbrush handle according to claim 14, wherein the control device has a means for changing an oscillation amplitude and/or an oscillation frequency of the drive motor, as a function of the signal of the transverse load recording device.

16. An electric toothbrush with a toothbrush handle according to claim 1 and a brush attachment having a bristle array mounted to the drive transmitter of the toothbrush handle.

17. The toothbrush according to claim 16, wherein the rotational point, defined by the bearing device, for the drive transmitter, lies in a brush tube section of the brush attachment placed on the toothbrush handle, between a bristle array of the brush attachment and on an end of the brush attachment on the handle side.

18. The toothbrush according to claim 16, wherein the rotational point, defined by the bearing device, for the drive transmitter, lies in the area of the center of mass of an oscillation system, which is formed by the moving parts of the toothbrush.

19. The toothbrush according to claim 16, wherein the drive transmitter, together with the brush attachment mounted thereon, forms a drive train capable of oscillation, and the drive motor and the bearing device are designed in a manner such that two oscillating nodes form along the aforementioned drive train.

20. The toothbrush according to claim 19, wherein the drive train capable of oscillation further comprises a drive part, which connects the drive motor to the drive transmitter, as well as a drive magnet of the drive motor.

21. The toothbrush according to claim 19, wherein the bearing device is designed such that the rotational point, defined by the bearing device, for the drive transmitter lies in the area of one of the two oscillating nodes.

22. The toothbrush according to claim 19, wherein the drive train forms a resonance oscillating body, which can be stimulated by the drive motor into a state of resonance oscillation, in which the bristle array of the brush attachment and the drive motor oscillate in phase equalization.

* * * * *